US00PP11480P

United States Patent [19]

Fazari

[11] Patent Number: Plant 11,480

[45] Date of Patent: Aug. 15, 2000

[54] HYBRID TEA ROSE PLANT NAMED 'FAZCANNE'

[75] Inventor: Evelyne Fazari, Antibes, France

[73] Assignee: Bear Creek Gardens, Inc., Medford, Oreg.

[21] Appl. No.: 09/203,790

[22] Filed: Dec. 1, 1998

[51] Int. Cl.[7] ..... A01N 5/00

[52] U.S. Cl. ..... Plt./140

[58] Field of Search ..... Plt./139, 140

*Primary Examiner*—Howard J. Locker

*Attorney, Agent, or Firm*—Klarquist Sparkman Campbell Leigh & Whinston, LLP

[57] ABSTRACT

Hybrid tea rose plant having long stems; dark green, healthy foliage; bright red flowers; good cut flower production; good vase life; and good shipping ability.

1 Drawing Sheet

The present invention relates to a new and distinct variety of rose plant of the hybrid tea class which was originated by me by crossing PEKOM ECLI (not patented), with A 0121 (Rosaplant seedling—not patented).

The primary objective of this breeding was to produce a new rose variety having long stems; dark green, healthy foliage; bright red flowers; good cut flower production; good vase life; and good shipping ability. The objective was substantially achieved, along with other desirable improvements, as evidenced by the following unique combination of characteristics that are outstanding in the new variety and that distinguish it from its parents, as well as from all other varieties of which I am aware:

1. Bright red, non-fading flowers;
2. Long stems;
3. Glossy, dark green foliage;
4. Good cut flower production;
5. Good shipping ability; and
6. Good vase life.

'FAZcanne' was bred and tested as a greenhouse cut flower rose. Production per square meter of greenhouse in Somis, Calif., is 170 stems. Stems average 24–28" long. Vase life is between 11–12 days. Transport of flowers over long distance (France to California) by air freight has indicated that 'FAZcanne' ships and rehydrates very well.

Asexual reproduction of this new variety by budding, as performed at Somis and Wasco, Calif., shows that the foregoing and all other characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) Colour Chart, except where ordinary dictionary significance of color is indicated.

Parentage:

*Seed parent.*—PEKOM ECLI (not patented).

*Pollen parent.*—A 0121 (Rosaplant seedling—not patented).

Classification:

*Botanical.*—Rosa hybrida.

*Commercial.*—Hybrid tea.

FLOWER

Observations made from specimens grown in a greenhouse environment at Somis, Calif. from January 1997 to September 1998.

Blooming habit: Continuous.

Bud:

*Size.*—Two inches long when the petals start to unfurl.

*Form.*—The bud form is long, pointed ovoid.

*Color.*—When sepals first divide, bud color is Red Group 46A. When half blown, the upper sides of the petals are Red Group 46B, and the lower sides of the petals are Red Group 46A.

*Sepals.*—color: Green Group 138B. Surface texture: Covered in fine hairs. There are three normally appendaged sepals. There are two unappendaged sepals with hairy edges.

*Receptacle.*—Color: Green Group 137B. Shape: Funnel. Size: Large (7/16" long ×¼" wide). Surface: Smooth.

*Peducle.*—Length: Long (4 to 4½"). Surface: Smooth, with a few flands and occasional small prickles. Color: Green Group 137B. Strength: Stiff, erect.

Bloom:

*Size.*—Large. Average open size is 4 to 4½".

*Borne.*—Singly.

*Stems.*—Strong. Average length is 24 to 28".

*Form.*—When first open: High centered. Performanence: Retains its form to the end; outer petals curl back with some quilling.

*Petalage.*—Number of petals under normal conditions: 35.

*Color.*—The upper sides of the petals are Red Group 46B. The reverse sides of the petals are Red Group 46A. The base of each petal has a Yellow Group 7C half moon (3/16"×3/16") at the point of attachment. The major color on the upper side is Red Group 46B.

*Variegations.*—Occasional whitish streaks on the guard petals.

*Discoloration.*—At the end of the first day: No change. At the end of the third day: No change through day six on the plant, then the color fades to Red Group 53B. In the vase, there is no change until day 10 when the color changes to Red Group 53B.

*Frangrance.*—None.

Petals:

*Texture.*—Thick, leathery.

*Shape.*—Round.

*Form.*—Tips slightly recurved, edges slightly quilled.
*Arrangement.*—Imbricated. No petaloids in the center.
*Persistence.*—Drop off cleanly before drying.
*Lastingness.*—On the plant: Long (eight days). As a cut flower: Long (11–12 days).

Reproductive parts:
*Anthers.*—Size: Large. Quantity: Many. Color: Yellow. Arrangement: Regular around styles.
*Filaments.*—Color: Reddish.
*Pollen.*—Color: Lemon-yellow.
*Styles.*—Color: Greenish-white.
*Stigmas.*—Color: Greenish-white.

Plant:
*Form.*—Bush.
*Growth.*—Vigorous; upright; branching; Height after six months growing in a greenhouse is 5½ feet and the width is 3½ feet.

Foliage: Number of leaflets on normal mid-stem leaves: Five.
*Size.*—Large. (5¾" long×4½" wide).
*Quantity.*—Abundant.
*Color.*—New foliage: Upper surface and lower surface: Greyed-purple Group 184B. Old foliage: Upper surface: Green Group 139A. Lower surface: Green Group 139C.
*Shape.*—Broadly oval.
*Texture.*—Upper side: Leathery, glossy.
*Edge.*—Serrated.
*Serration.*—Single, small.
*Petiole rachis.*—Color: Green Group 137C.
*Petiole underside.*—Smooth with an occasional prickle.
*Stipules.*—Long (¾"); serrated, bearded.
*Disease resistance.*—Resistant to mildew in a greenhouse. Not tested for blackspot or rust.

Wood:
*New wood.*—Color: Greyed-purple Group 184B. Bark: Smooth.
*Old wood.*—Color: Green Group 137A. Bark: Smooth.

Prickles:
*Quantity.*—On main canes from base: Ordinary. On laterals from main canes: Ordinary.
*Form.*—Medium; hooked slightly downward.
*Color when young.*—Greyed-purple Group 184B.
*Color when mature.*—Greyed-orange Group 164D.

Small prickles:
*Quantity.*—On main stalks: Few. On laterals: Few.

I claim:

1. A new and distinct variety of rose plant of the hybrid tea class, substantially as herein shown and described, characterized particularly as to novelty by its long stems; dark green, healthy foliage; bright red flowers; good cut flower production; good vase life; and good shipping ability.

* * * * *

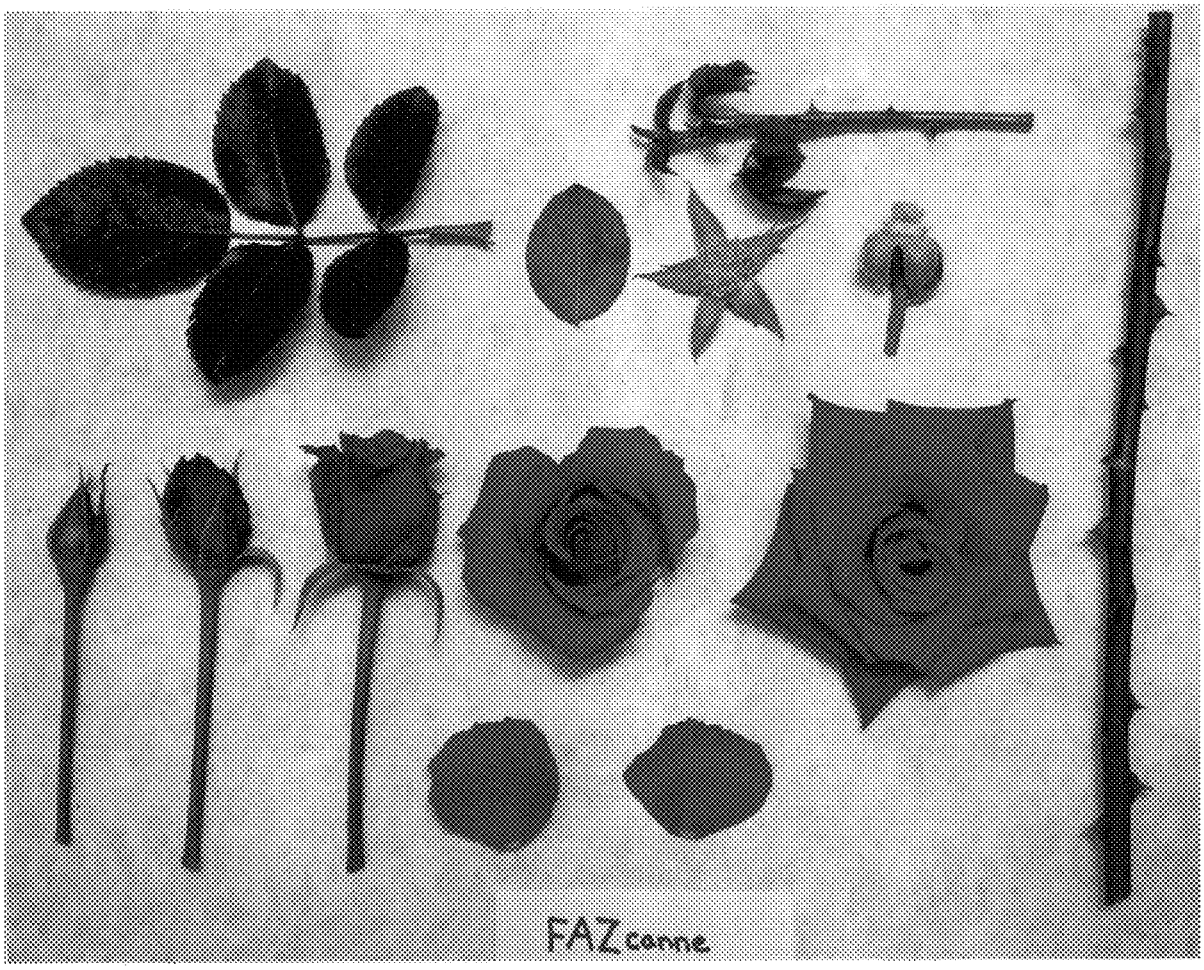
FAZ corne